US005661174A

United States Patent [19]
Naumann et al.

[11] Patent Number: 5,661,174
[45] Date of Patent: Aug. 26, 1997

[54] GUANIDINEALKYL-1,1-BISPHOSPHONIC ACID DERIVATIVES, PROCESS FOR THEIR PREPARATION AND THEIR USE

[75] Inventors: Christoph Naumann, Niedernhausen; Hans-Jochen Lang, Hofheim/Taunus; Jürgen Sandow, Glashütten, all of Germany; Anne-Marie Moura, Paris, France

[73] Assignee: Hoechst Aktiengesellschaft, Frankfurt am Main, Germany

[21] Appl. No.: 609,473

[22] Filed: Mar. 1, 1996

Related U.S. Application Data

[62] Division of Ser. No. 346,239, Nov. 23, 1994, Pat. No. 5,498,617, which is a division of Ser. No. 159,119, Nov. 30, 1993, Pat. No. 5,395,826.

[30] Foreign Application Priority Data

Dec. 2, 1992 [DE] Germany ............ 42 40 422.3
May 13, 1993 [DE] Germany ............ 43 16 019.0
Sep. 23, 1993 [DE] Germany ............ 43 32 362.6

[51] Int. Cl.$^6$ ............................ A61K 31/40; C07F 9/40
[52] U.S. Cl. ............................ 514/416; 548/414; 548/415
[58] Field of Search ............................ 548/414, 415; 514/416

[56] References Cited

U.S. PATENT DOCUMENTS

| | | |
|---|---|---|
| 4,255,572 | 3/1981 | Kruger et al. . |
| 4,927,814 | 5/1990 | Gall et al. . |
| 4,942,157 | 7/1990 | Gall et al. . |
| 5,294,608 | 3/1994 | Lang et al. . |
| 5,395,826 | 3/1995 | Nauman et al. . |

FOREIGN PATENT DOCUMENTS

| | | |
|---|---|---|
| 2085171 | 6/1993 | Canada . |
| 0 010 147 A1 | 4/1980 | European Pat. Off. . |
| 0 186 405 A3 | 7/1986 | European Pat. Off. . |
| 0 252 504 A1 | 1/1988 | European Pat. Off. . |
| 0 298 553 A1 | 1/1989 | European Pat. Off. . |
| 0 416 499 A2 | 3/1991 | European Pat. Off. . |
| 0 546 548 A1 | 6/1993 | European Pat. Off. . |

OTHER PUBLICATIONS

"New Methods of Preparative Organic Chemistry IV, Synthesis Using Heterocyclic Amides (Azolides)", Staab, H.A., Angew. Chem. Internat. Edit. 1(7):351–367 (1962).
Advanced Organic Chemistry—Reactions, Mechanisms, and Structure March J., Fourth Edition, pp. 348–352. (1992).
"Zur Guanylierung von Aminen mit O–Methyl–Isoharnstoff–Sulfat", Weiss et al., Chemiker–Zeitung, 98(12):617–621 (1974).

Primary Examiner—Johann Richter
Assistant Examiner—John Peabody
Attorney, Agent, or Firm—Finnegan, Henderson, Farabow, Garrett & Dunner, L.L.P.

[57] ABSTRACT

Compounds of the tautomeric formula Ia, Ib or Ic, where R is a radical of the formula are effective compounds for the treatment and prophylaxis of degenerative bone disorders. They are used as pharmaceuticals.

6 Claims, No Drawings

GUANIDINEALKYL-1,1-BISPHOSPHONIC ACID DERIVATIVES, PROCESS FOR THEIR PREPARATION AND THEIR USE

This is a division of application Ser. No. 08/346,239, filed Nov. 23, 1994, now U.S. Pat. No. 5,498,617 which is a division of application Ser. No. 08/159,119, filed Nov. 30, 1993, now U.S. Pat. No. 5,395,826.

The therapy of disorders of the bone system is becoming increasingly important. Thus, for example, osteoporosis is a common bone disorder. In the various types of osteoporosis there is great loss of bone tissue so that finally the mechanical stability of the bone is lost. In healthy people the rate at which osteoclasts and osteoblasts are formed is designed to keep bone formation and bone resorption in equilibrium. The equilibrium is disturbed in osteoporosis so that bone destruction occurs.

It is already known that guanidinealkyl-1,1-bisphosphonic acid derivatives are suitable for the prophylaxin and/or treatment of osteoporosis (EP 0 546 548).

In the effort to obtain further active compounds for the treatment and prophylaxis of osteoporosis with few side effects, it has now been found that the guanidinealkyl-1,1-bisphosphonic acids according to the invention reduce bone resorption.

The invention, therefore relates to a compound of the tautomeric formula Ia, Ib or Ic

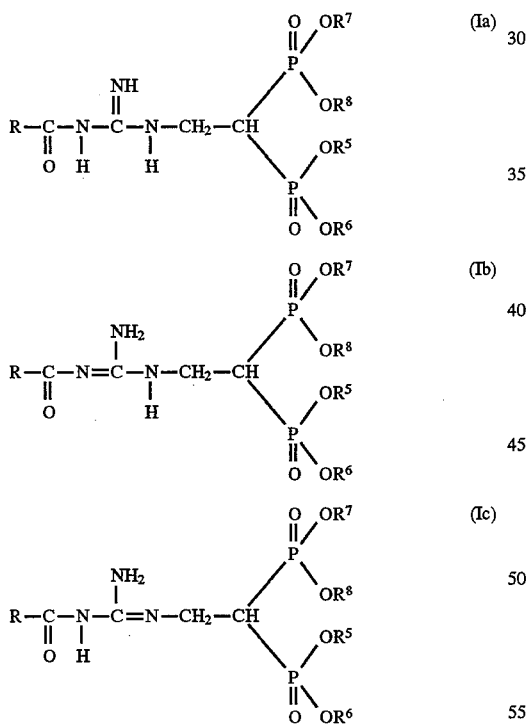

and/or a physiologically tolerated salt of the compound of the formula Ia, Ib or Ic;

R has the following meaning therein:

I) a radical of the formula V

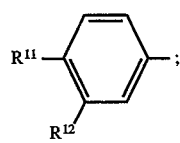

wherein $R^{11}$ or $R^{12}$ has the following meaning:

a) $R^{13}$—S(O)$_n$— or b) 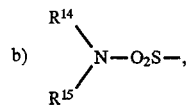

where $R^{13}$ is
1) $(C_1-C_6)$-alkyl,
2) $(C_5-C_7)$-cycloalkyl,
3) cyclopentylmethyl,
4) cyclohexylmethyl,
5) phenyl,
6) phenyl substituted once to three times by
   6.1 fluorine atom,
   6.2 chlorine atom,
   6.3 methyl or
   6.4 methoxy, where n is the integer zero, 1 or 2, where $R^{14}$ and $R^{15}$ are identical or different and have, independently of one another, the following meaning:
1) hydrogen atom,
2) $(C_1-C_6)$-alkyl,
3) phenyl,
4) phenyl substituted once or twice by
   4.1 fluorine atom,
   4.2 chlorine atom,
   4.3 methyl or
   4.4 methoxy,
5) —(CH$_2$)$_m$-phenyl where m is an integer from 1 to 4, or
6) —(CH$_2$)$_m$-phenyl where m is an integer from 1 to 4 and the phenyl radical is substituted once or twice by the radicals indicated in 4.1 to 4.4,
7) $R^{14}$ and $R^{15}$ together form a straight-chain or branched chain of 4 to 7 carbon atoms, the chain can additionally be interrupted by
   7.1 O,
   7.2 S or
   7.3 NR$^{10}$ where
      $R^{10}$ is 1) hydrogen atom or 2) methyl, or
8) $R^{14}$ and $R^{15}$ form together with the nitrogen atom to which they bonded a
   8.1 dihydroindole,
   8.2 tetrahydroquinoline or
   8.3 tetrahydroisoquinoline ring, and the other substituent $R^{11}$ or $R^{12}$ in each case means
a) hydrogen atom,
b) halogen atom, such as fluorine, chlorine, bromine or iodine atom,
c) $(C_1-C_4)$-alkyl,
d) $(C_1-C_4)$-alkoxyl,
e) phenoxy,
f) phenoxy substituted once to three times by
   1) fluorine or chlorine atom,
   2) methyl or
   3) methoxy,
g) $R^{13}$—S(O)$_n$, where n is the integer zero, 1 or 2 and $R^{13}$ has the abovementioned meaning, or h) 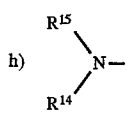

where $R^{14}$ and $R^{15}$ have the abovementioned meaning, or

II) a radical of the formula VI

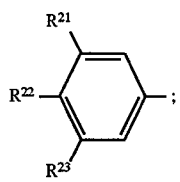 (VI)

wherein $R^{21}$, $R^{22}$ or $R^{23}$ has the following meaning:
a) hydrogen atom,
b) halogen atom, such as fluorine, chlorine, bromine or iodine atom, or
c) $(C_1-C_{12})$-alkyl,
where one of the substituents $R^{21}$, $R^{22}$ or $R^{23}$ can also mean
1) $N_3$,
2) CN,
3) OH,
4) $(C_1-C_{10})$-alkoxy,
5) $R^{24}-C_nH_{2n}-O_m-$, where
m is the number zero or 1,
n is the number zero, 1, 2 or 3,
$R^{24}$ is
1) $C_pF_{2p+1}$ where
p is the number 1, 2 or 3, as long as n is the number zero or 1,
2) $(C_3-C_{12})$-cycloalkyl,
3) phenyl,
4) pyridyl,
5) quinolyl or
6) isoquinolyl,
where the ring system in the radicals 3) to 6) is unsubstituted or substituted by a radical from the group
3.1 fluorine atom,
3.2 chlorine atom,
3.3 $CF_3$,
3.4 methyl,
3.5 methoxy or
3.6 $NR^{25}R^{26}$ where
$R^{25}$ and $R^{26}$ are identical or different and have, independently of one another, the meaning
3.6.1 hydrogen atom or
3.6.2 $(C_1-C_4)$-alkyl, or III) a radical of the formula VII

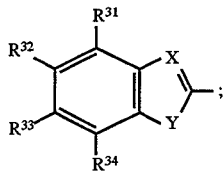 (VII)

wherein $R^{31}$, $R^{32}$, $R^{33}$ or $R^{34}$ has the following meaning:
a) hydrogen atom,
b) halogen atom, such as fluorine, chlorine, bromine or iodine atom, or c) —CN,
d) —$NO_2$,
e) —$N_3$,
f) —$(C_1-C_6)$-alkyl, straight-chain or branched or
g) $R^{35}-C_nH_{2n}-Z-$,
where n is the number zero, 1, 2, 3, 4, 5 or 6, and the alkylene chain —$C_nH_{2n}$— is straight-chain or branched, and one carbon atom can be replaced by an oxygen, sulfur or nitrogen atom,
$R^{35}$ is
1) hydrogen atom,
2) $(C_3-C_6)$-alkenyl,
3) $(C_5-C_8)$-cycloalkyl,
4) $(C_5-C_8)$-cycloalkyl, substituted by a hydroxyl group, or one methylene group is replaced by an oxygen, sulfur or nitrogen atom, or
5) phenyl, unsubstituted or substituted by
1 to 3 radicals from the group
5.1 halogen atom such as fluorine, chlorine, bromine or iodine atom,
5.2 $CF_3$,
5.3 $CH_3-S(O)_x$, where x is the number zero, 1 or 2,
5.4 $R^{36}-W_y$ where $R^{36}$ is hydrogen atom, methyl or ethyl, W is oxygen atom, NH or $NCH_3$, and y is zero or 1,
5.5 $C_mF_{2m+1}$, where m is the number 1, 2 or 3,
5.6 pyridyl,
5.7 quinolyl or
5.8 isoquinolyl,
Z is
1) —CO—,
2) —$CH_2$—,
3) —$[CH(OH)]_q$—, where q is the number 1, 2 or 3,
4) —$[C(CH_3)(OH)]_q$—, where q is the number 1, 2 or 3,
5) —O—,
6) —NH—, 7) 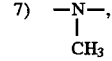

8) —$S(O)_x$—, where x is zero, 1 or 2,
9) —$SO_2$—NH— or

10) 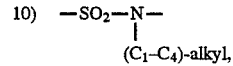

X has the following meaning
a) N or
b) C—$R^{37}$, where $R^{37}$ is hydrogen atom, $(C_1-C_4)$-alkyl or $(C_2-C_4)$-alkenyl,
Y has the following meaning
a) NH,
b) —N—$(C_1-C_6)$-alkyl,
c) —N—$(C_2-C_4)$-alkenyl or
d) $R^{35}-C_nH_{2n}-Z-$, where $R^{35}$, n and Z are defined as under g),
$R^5$, $R^6$, $R^7$ and $R^8$ are identical or different and have, independently of one another, the following meaning
a) hydrogen atom,
b) $(C_1-C_5)$-alkyl, straight-chain or branched, or
c) phenyl.

If the substituents $R^{11}$, $R^{12}$, $R^{21}$, $R^{22}$, $R^{23}$, $R^{24}$, $R^{25}$, $R^{26}$, $R^{31}$, $R^{32}$, $R^{33}$, $R^{34}$ and $R^{35}$ contain one or more centers of asymmetry, the invention embraces both compounds with the S and those with the R configuration. The compounds can be in the form of optical isomers, diastereoisomers, racemates or mixtures thereof.

The defined alkyl radicals can be both straight-chain and branched.

A preferred compound of the formula Ia, Ib or Ic, and/or a physiologically tolerated salt of the compound of the formula Ia, Ib or Ic is one where R has the following meaning:

I) a radical of the formula V wherein $R^{11}$ has the following meaning:
  a) fluorine atom,
  b) chlorine atom, c) 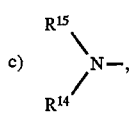

where $R^{14}$ and $R^{15}$ have the above-mentioned meaning,
  d) $R^{13}$—S(O)$_n$—, where n is zero, 1 or 2, or
  e) phenoxy,
where $R^{12}$ has the following meaning:
  a) $R^{13}$—S(O)$_n$, where n is zero, 1 or 2, or b) 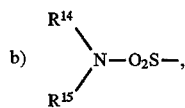

where $R^{14}$ and $R^{15}$ have above-mentioned meaning, or

II) a radical of the formula VI where $R^{21}$, $R^{22}$ or $R^{23}$ has the following meaning:
  a) hydrogen atom,
  b) halogen atom, such as fluorine, chlorine or bromide atom, or
  c) (C$_1$–C$_8$)-alkyl,
where one of the substitients $R^{21}$, $R^{22}$ or $R^{23}$ can also mean
  1) OH,
  2) (C$_1$–C$_6$)-alkoxy,
  5) $R^{24}$—C$_n$H$_{2n}$—O$_m$, where
    m is the number zero or 1,
    n is the number zero, 1, 2 or 3,
    $R^{24}$ means
      1) C$_p$F$_{2p+1}$ where
        p is the number 1 as long as
        n is the number zero or 1,
      2) (C$_5$–C$_7$)-cycloaklyl,
      3) phenyl,
      4) pyridyl,
      5) quinolyl or
      6) isoquinolyl,
    where the ring system in the radicals 3) to 6) is unsubstituted or substituted by a radical from the group
      3.1 fluorine atom,
      3.2 chlorine atom,
      3.3 CF$_3$,
      3.4 CH$_3$ or
      3.5 methoxy, or III) a radical of the formula VII wherein $R^{31}$, $R^{32}$, $R^{33}$ or $R^{34}$ has the following meaning:
  a) hydrogen atom,
  b) halogen atom, such as fluorine, chlorine, bromine or iodine atom, or
  c) (C$_1$–C$_6$)-alkyl, straight-chain or branched, or
  d) $R^{35}$—C$_n$H$_{2n}$—Z—, where
    n is the number zero, 1 or 2, and the alkylene chain —C$_n$H$_{2n}$— is straight-chain or branched, and one carbon atom can be replaced by an oxygen, sulfur or nitrogen atom,
    $R^{35}$ is
      1) hydrogen atom,
      2) (C$_5$–C$_8$)-cyckoalkyl,
      3) (C$_5$–C$_8$)-cycloalkyl, substituted by hydroxyl group, or one methylene group is replaced by an oxygen, sulfur or nitrogen atom, or
      4) phenyl, unsubstituted or substituted by 1 to 3 radicals from the group
        4.1 halogen atom such as fluorine, chlorine, bromine or iodine atom,
        4.2 CF$_3$,
        4.3 CH$_3$—S(O)$_x$, where x is the number Zero, 1 or 2,
        4.4 $R^{36}$—W$_y$ where $R^{36}$ is hydrogen atom, methyl or ethyl, W is oxygen atom, NH or NCH$_3$, and y is zero or 1,
        4.5 C$_m$F$_{2m+1}$, where m is the number 1, 2 or 3,
        4.6 pyridyl,
        4.7 quinolyl or
        4.8 isoquinolyl,
    Z is
      1) —CO—,
      2) —CH$_2$—,
      3) —[CH(OH)]$_q$—, where q is the number 1, 2 or 3,
      4) —[C(CH$_3$)(OH)]$_q$—, where q is the number 1, 2 or 3,
      5) —O— or
      6) —S(O)$_x$—, where x is zero, 1 or 2,
    X has the following meaning
      a) N or
      b) CH,
    Y has the following meaning
      a) —N—(C$_1$–C$_6$)-alkyl,
      b) —N—(C$_2$–C$_4$)-alkenyl or
      c) $R^{35}$—C$_n$H$_{2n}$—Z—, where $R^{35}$, n and Z are defined as under d),
    $R^5$, $R^6$, $R^7$ and $R^8$ are identical or different and have, independently of one another, the following meaning
      a) hydrogen atom,
      b) (C$_1$–C$_5$)-alkyl, straight-chain or branched.

A compound of the formula Ia, Ib or Ic where $R^{11}$ has the following meaning:

a) 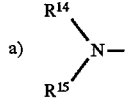

where $R^{14}$ and $R^{15}$ are identical or different and have, independently of one another, the following meaning
  1) hydrogen atom or
  2) (C$_1$–C$_4$)-alkyl, or
$R^{14}$ and $R^{15}$ together form a (C$_4$–C$_7$)-alkyl chain, or
b) $R^{13}$—S— where
  $R^{13}$ is
    a) phenyl, or
    b) phenyl, substituted by chlorine in the para position,
where $R^{12}$ has the following meaning:
  a) CH$_3$—SO$_2$—, b) H₂N—SO₂—,
c) phenoxy or
d) phenoxy, substituted by chlorine in the para position, $R^5$, $R^6$, $R^7$ and $R^8$ are identical or different and have, independently of one another, the following meaning
a) hydrogen atom or
b) (C₁-C₄)-alkyl, and physiologically tolerated salts of the compound of the formula Ia, Ib or Ic are particularly preferred.

Especially preferred are: tetraethyl 2-[(1-methyl-2-indolylcarbonyl)-(aminoiminomethyl)amino]ethane-1,1-bisphosphonate, 2-[(1-methyl-2-indolylcarbonyl)-(aminoiminomethyl)amino]ethane-1,1-bisphosphonic acid, 2-[(3-methylsulfonyl-4-piperidylbenzoyl)-(aminoiminomethyl)amino]ethane-1,1-bisphosphonic acid, tetraethyl 2-[(3-methylsulfonyl-4-piperidylbenzoyl)-(aminoiminomethyl)amino]ethane-1,1-bisphosphonate, tetraethyl 2-[(3,5-dichlorobenzoyl)-(aminoiminomethyl) amino]ethane-1,1-bisphosphonate and 2-[(3,5-dichlorobenzoyl)-(aminoiminomethyl)amino]ethane-1,1-bisphosphonic acid.

The compounds according to the invention can be prepared, for example, as follows:

A compound of the formula IV

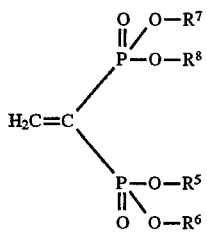

(IV)

where $R^5$, $R^6$, $R^7$ and $R^8$ have the meaning mentioned in formula Ia, is A) reacted with a compound of the formula III

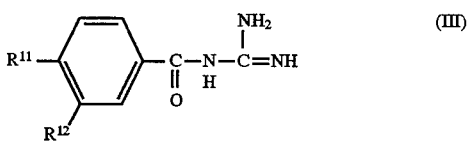

(III)

in the presence of an inert solvent to give a compound of the formula Ia, Ib or Ic, where $R^{11}$ and $R^{12}$ have the meaning mentioned in formula Ia, Ib or Ic, and, where appropriate, B) the bisphosphonic ester of the compound of the formula Ia, Ib or Ic is converted into the corresponding bisphosphonic acid, or a compound of the formula IV, where $R^5$, $R^6$, $R^7$ and $R^8$ have the meaning mentioned in formula Ia, is C) reacted with a compound of the formula VIII

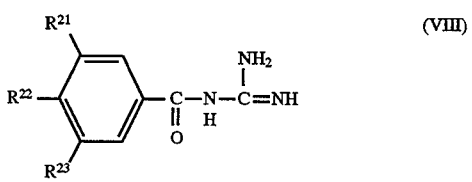

(VIII)

in the presence of an inert solvent to give a compound of the formula Ia, Ib or Ic, where $R^{21}$, $R^{22}$ and $R^{23}$ have the meaning mentioned in formula Ia, Ib or Ic, and, where appropriate, D) the bisphosphonic ester of the compound of the formula Ia, Ib or Ic is converted into the corresponding bisphosphonic acid, or a compound of the formula IV, where $R^5$, $R^6$, $R^7$ and $R^8$ have the meaning mentioned in formula Ia, is E) reacted with a compound of the formula IX

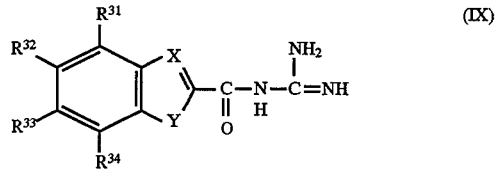

(IX)

in the presence of an inert solvent to give a compound of the formula Ia, Ib or Ic, where $R^{31}$, $R^{32}$, $R^{33}$ and $R^{34}$ have the meaning mentioned in formula Ia, Ib or Ic, and, where appropriate, F) the bisphosphonic ester of the compound of the formula Ia, Ib or Ic is converted into the corresponding bisphosphonic acid.

The best procedure for process variant A) is to react the compound of the formula III in equimolar amount or in an up to three-fold excess, where appropriate in an inert solvent such as dimethyl sulfoxide (DMSO), dimethylformamide (DMF), toluene, (C₁-C₄)-alkanol, tetrahydrofuran (THF), dioxane or diethyl ether, with a compound of the formula IV with the addition of a base such as potassium carbonate, sodium carbonate, potassium hydroxide, triethylamine, diethylamine or alternatively also without addition of a base to give a compound of the formula Ia, Ib or Ic. The reaction temperatures are about 25° C. to 100° C., and when a solvent is used preferably between about 25° C. and the boiling point of the solvent, in particular at 70° C. The reaction times are from 6 to 48 hours, preferably 12 to 24 hours. The completion of the reaction can be determined, for example, by thin-layer chromatography.

To isolate and to purify the reaction products of the formula Ia, Ib or Ic, the reaction mixture can be purified on a silica gel column with an eluent mixture of ethyl acetate and alcohol, ratio 6:1 by volume for example. The resulting compounds of the formula Ia, Ib or Ic can be converted into the corresponding bisphosphonic acids by hydrolysis (process variant B), for example by heating under reflux in concentrated hydrochloric acid, or by treatment with strong acids or trimethylsilyl halide in an anhydrous solvent and subsequent hydrolysis. Anhydrous hydrobromic acid in acetic acid can be used directly or after appropriate dilution, or trimethylsilyl iodide dissolved in a solvent such as tetrachloromethane, dimethylformamide, chloroform or toluene is used. The hydrolysis can be carried out with cooling or heating, for example the ester can be reacted with a trimethylsilyl halide while cooling at −10° C., or below, and a partially hydrolyzed product is obtained.

The starting compounds of process variant A) can be prepared for the compounds III and IV in a simple way by processes known from the literature (EP 0 298 553; EP 0 416 499).

The best procedure for process variant C) is to react the compound of the formula VIII in equimolar amount or in an up to three-fold excess, where appropriate in an inert solvent such as dimethyl sulfoxide (DMSO), dimethylformamide (DMF), toluene, (C₁-C₄)-alkanol, tetrahydrofuran (THF), dioxane or diethyl ether, with a compound of the formula IV with the addition of a base such as potassium carbonate, sodium carbonate, potassium hydroxide, triethylamine, diethylamine or alternatively also without addition of a base to give a compound of the formula Ia, Ib or Ic. The reaction temperatures are about 25° C. to 100° C., and when a solvent is used preferably between about 25° C. and the boiling point of the solvent, in particular at 70° C. The reaction times are from 6 to 48 hours, preferably 12 to 24 hours. The completion of the reaction can be determined, for example, by thin-layer chromatography.

To isolate and to purify the reaction products of the formula Ia, Ib or Ic, the reaction mixture can be purified on a silica gel column with an eluent mixture of ethyl acetate and alcohol, ratio 6:1 by volume for example. The resulting compounds of the formula Ia, Ib or Ic can be converted into the corresponding bisphosphonic acids by hydrolysis (process variant D), for example by heating under reflux in concentrated hydrochloric acid, or by treatment with strong acids or trimethyisilyl halide in an anhydrous solvent and subsequent hydrolysis. Anhydrous hydrobromic acid in acetic acid can be used directly or after appropriate dilution, or trimethylsilyl iodide dissolved in a solvent such as tetrachloromethane, dimethylformamide, chloroform or toluene is used. The hydrolysis can be carried out with cooling or heating, for example the ester can be reacted with a trimethylsilyl halide while cooling at $-10°$ C. or below, and a partially hydrolyzed product is obtained.

The starting compounds of process variant C) can be prepared for the compound of the formula IV in a simple way by processes known from the literature (EP 0 298 553; EP 0 416 499).

The compounds of the formula VIII can be prepared by reacting a compound of the formula II

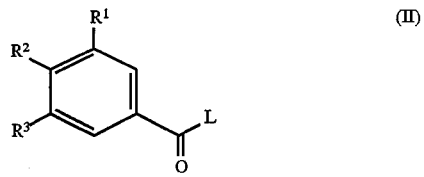

with guanidine, in which $R^1$ to $R^3$ have the stated meaning, and L is a leaving group which easily undergoes nucleophilic substitution.

The activated acid derivatives of the formula II in which L is an alkoxy, preferably a methoxy group, a phenoxy group, phenylthio, methylthio, 2-pyridylthio group, a nitrogen heterocycle, preferably 1-imidazolyl, are advantageously obtained in a manner known per se from the carbonyl chlorides on which they are based (formula II, L=Cl), which for their part in turn can be prepared in a manner known per se from the carboxylic acids on which they are based (formula II, L=OH), for example with thionyl chloride. Besides the carbonyl chlorides of the formula II (L=Cl), it is also possible to prepare other activated acid derivatives of the formula II in a manner known per se directly from the benzoic acid derivatives on which they are based (formula II, L=OH), such as, for example, the methyl esters of the formula II with L=OCH$_3$, by treatment with gaseous HCl in methanol, the imidazolides of the formula II by treatment with carbonyldiimidazole (L=1-imidazolyl, Staab, Angew. Chem. Int. Ed. Engl. 1, 351–367 (1962)), the mixed anhydrides II with Cl—COOC$_2$H$_5$ or tosyl chloride in the presence of triethylamine in an inert solvent, as well as the activation of benzoic acids with dicyclohexylcarbodiimide (DCC) or with O-[(cyano(ethoxycarbonyl)methylene) amino]-1,1,3,3-tetramethyluronium tetrafluoroborate ("TOTU") (Weiss and Krommer, Chemiker Zeitung 98, 817 (1974)). A number of suitable methods for the preparation of activated carboxylic acid derivatives of the formula II are indicated in J. March, Advanced Organic Chemistry, Third Edition (John Wiley & Sons, 1985), page 350, with indication of source literature.

The reaction of an activated carboxylic acid derivative of the formula II with guanidine takes place in a manner known per se in a protic or aprotic polar but inert organic solvent.

In this connection, methanol or THF at between 20° C. and the boiling point of these solvents has proven suitable in the reaction of the methyl benzoates (II, L=OMe) with guanidine. Most of the reactions of compounds II with salt-free guanidine were advantageously carried out in aprotic inert solvents such as THF, dimethoxyethane and dioxane. However, it is also possible to use water as solvent when a base such as, for example, NaOH is used in the reaction of II.

If L=Cl, the addition of an acid trap is advantageous, for example in the form of excess guanidine to bind the hydrohalic acid.

Some of the basic benzoic acid derivatives of the formula II are known and described in the literature. The unknown compounds of the formula II can be prepared by methods known from the literature.

Carboxylic acids or their esters of the formula II (for example L=—OH or —O-methyl) with $R^2$ meaning halogen or $R^3$ meaning nitro are versatile starting compounds which can be used for further carboxylic acids of the formula II, where the halogen in the position of $R^2$ is very conveniently replaced in a manner known per se by a large number of nucleophilic reagents such as phenols or alcohols $R^4$—$C_nH_{2n}$—OH or their alkali metal salts to form corresponding benzoic acid derivatives. It is likewise possible for nitro groups after reduction to the corresponding aminobenzoic acid to lead by Sandmeier or Ullmann reactions to desired, in particular halogen-substituted, benzoic acid derivatives. Chlorine, bromine or iodine can also in many cases be introduced into a particular benzoic acid by direct halogenation using a Friedel-Crafts catalyst in a manner known per se.

The best procedure for process variant E) is to react the compound of the formula IX in equimolar amount or in an up to three-fold excess, where appropriate in an inert solvent such as dimethyl sulfoxide (DMSO), dimethylformamide (DMF), toluene, ($C_1$-$C_4$)-alkanol, tetrahydrofuran (THF), dioxane or diethyl ether, with a compound of the formula IV with the addition of a base such as potassium carbonate, sodium carbonate, potassium hydroxide, triethylamine, diethylamine or alternatively also without addition of a base to give a compound of the formula Ia, Ib or Ic. The reaction temperatures are 25° C. to 100° C., and when a solvent is used the reaction temperatures are preferably from 25 C. to the boiling point of the solvent, in particular at 70° C. The reaction times are from 6 to 48 hours, preferably 12 to 24 hours. The completion of the reaction can be determined, for example, by thin-layer chromatography.

To isolate and to purify the reaction products of the formula Ia, Ib or Ic, the reaction mixture can be purified on a silica gel column with an eluent mixture of ethyl acetate and/or alcohol, ratio 6:1 by volume for example. The resulting compounds of the formula Ia, Ib or Ic can be converted into the corresponding bisphosphonic acids by hydrolysis (process variant F), for example by heating under reflux in concentrated hydrochloric acid, or by treatment with strong acids or trimethylsilyl halide in an anhydrous solvent and subsequent hydrolysis. Anhydrous hydrobromic acid in acetic acid can be used directly or after appropriate dilution, or trimethylsilyl iodide dissolved in a solvent such as tetrachloromethane, dimethylformamide, chloroform or toluene is used. The hydrolysis can be carried out with cooling or heating, for example the ester can be reacted with a trimethylsilyl halide while cooling at $-10°$ C. or below, and a partially hydrolyzed product is obtained.

The starting compounds of process variant A) can be prepared for the compound of the formula IV in a simple way by processes known from the literature (EP 0 298 553; EP 0 416 499).

The compounds of the formula IX can be prepared in a known manner (DE 43 26 005.5).

The invention also relates to pharmaceuticals which contain at least an effective amount of at least one compound of the formula Ia, Ib or Ic and/or at least one of the physiologically tolerated salts of a compound of the formula Ia, Ib or Ic in addition to pharmaceutically suitable and physiologically tolerated ancillary substances and excipients, diluents and/or other active substances.

The invention furthermore relates to the use of the compounds of the formula Ia, Ib or Ic and/or their physiologically tolerated salts for the production of a pharmaceutical for the prophylaxis and treatment of degenerative disorders of the bone system.

The invention also relates to the use of the compounds of the formula Ia, Ib or Ic and/or their physiologically tolerated salts for the production of a pharmaceutical for the treatment of disorders with increased bone resorption, in particular metastatic osteocarcinoma, Paget's disease, hypercalcemia or osteoporosis.

The pharmaceuticals according to the invention can be administered superficially, percutaneously, nasally, intravenously, intramuscularly, intraperitoneally, subcutaneously, intraarticularly, periarticularly, rectally or orally.

The pharmaceuticals according to the invention for the prophylaxis and treatment of osteoporosis are produced by converting at least one compound of the formula Ia, Ib or Ic and/or one of its physiologically tolerated salts, where appropriate with ancillary substances and/or excipients, into a suitable dosage form. The ancillary substances and excipients are derived from the group of vehicles, preservatives and other customary ancillary substances.

The compound of the formula Ia, Ib or Ic can in this connection be used alone or together with pharmaceutical ancillary substances, in particular both in veterinary and in human medicine.

The ancillary substances which are suitable for the desired pharmaceutical formulation are familiar to the skilled worker on the basis of his expert knowledge. Besides solvents, gel formers, suppository bases, tablet ancillary substances and other active substance vehicles, it is possible to use, for example, antioxidants, dispersants, emulsifiers, antifoam agents, flavorings, preservatives, eolubilizers or colorants.

For a form for oral use, the active compounds are mixed with the additives suitable for this purpose, such as excipients, stabilizers or inert diluents, and converted by customary methods into the suitable dosage forms such as tablets, coated tablets, hard gelatin capsules, aqueous, alcoholic or oily solutions. Examples of inert vehicles which can be used are gum arabic, magnesia, magnesium carbonate, potassium phosphate, lactose, glucose or starch, especially corn starch. The preparation can take place in this case both as dry and as wet granules. Examples of suitable oily excipients or solvents are vegetable or animal oils, such as sunflower oil or fish liver oil.

For subcutaneous or intravenous administration, the active compounds are converted, if required with the substances customary for this purpose, such as solubilizers, emulsifiers or other ancillary substances, into a solution, suspension or emulsion. Examples of suitable solvents are: water, physiological saline or alcohols, for example ethanol, propanol, glycerol, as well as sugar solutions such as glucose or mannitol solutions, or else a mixture of the various solvents mentioned.

Examples of pharmaceutical formulations suitable for administration in the form of aerosols or sprays are solutions, suspensions or emulsions of the active substance of the formula Ia, Ib or Ic in a pharmaceutically acceptable solvent such as, in particular, ethanol or water, or a mixture of such solvents. The formulation can, if required, also contain other pharmaceutical ancillary substances such as surfactants, emulsifiers and stabilizers, as well as a propellant gas. A preparation of this type contains the active substance, normally in a concentration of 0.1 to 10, in particular of 0.3 to 3, % by weight.

The dosage of the active substance of the formula Ia, Ib or Ic which is to be administered, and the frequency of administration depend on the potency and duration of action of the compound used; in addition on the nature and severity of the disease to be treated and on the sex, age, weight and individual response of the mammal or human to be treated.

The dosage to be used of the pharmaceuticals according to the invention depends on various factors such as dosage form of the medicament and condition, weight and severity of the disorder of the patient. A daily dose of about 5,000 mg of the pharmaceuticals according to the invention should, however, be exceeded only temporarily. 10 to 2,500 mg are preferred as daily dose for a human with a body weight of 70 kg. Administration of the daily dose of the pharmaceuticals according to the invention can take place in the form of a single administration or in several small doses. Administration in 3 to 8 doses per day is preferred.

The invention is explained in detail by means of Examples hereinafter. Unless otherwise indicated, percentage data relate to percentages by volume.

EXAMPLE 1

Preparation of tetraethyl 2-[(3-methylsulfonyl-4-piperidylbenzoyl)-(aminoiminomethyl)amino]ethane-1,1-bisphosphonate 3.24 g (10 mmol) of (3-methylsulfonyl-4-piperidylbenzoyl)-(aminoiminomethyl)amine and 3.0 g (10 mmol) of tetraethyl vinyldiphosphonate are dissolved in 40 ml of absolute tetrahydrofuran. To this is added 0.5 g (3.6 mmol) of dry potassium carbonate, and the mixture is heated to boiling under protective gas for 3.5 hours. Subsequently a further 0.33 g (2.4 mmol) of potassium carbonate is added, and the mixture is heated to boiling for a further 2 hours. Subsequently the reaction mixture is stirred at room temperature for a further 16 hours. Filtration and removal of the solvent result in 4.5 g of crude substance. The substance is chromatographed on a silica gel column. The eluent used is ethyl acetate with 10% ethanol.

Yield: 3.2 g (52% of theory)

Melting point: 148° to 152° C.

$^{31}$P-NMR spectroscopy: (CDCl$_3$) δP=21.77 ppm

EXAMPLE 2

Preparation of 2-[(3-methylsulfonyl-4-piperidylbenzoyl)(aminoiminomethyl)amino]ethane-1,1-bisphosphonic acid 1.5 g (2.4 mmol) of tetraethyl 2-[(3-methylsulfonyl-4-piperidylbenzoyl)-(aminoiminomethyl)amino]ethane-1,1-bisphosphonate from Example 1 are dissolved in 60 ml of absolute dioxane at 60° C. The reaction mixture is subsequently allowed to reach room temperature, and 1.64 g (10.8 mmol) of bromotrimethylsilane are added. The mixture is stirred at room temperatures for 16 hours and subsequently heated at 60° C. for a further 4 hours. Solvent and volatiles are subsequently removed at 40° C./0.1 torr. 15 ml of water are then added to the residue, and the mixture is stirred at room temperature for 4 hours. The resulting residue is filtered off and washed several times with ethanol. The residue resulting from this is subsequently boiled in 20 ml of methanol and 10 ml of water.

Yield: 460 mg (38% of theory)

Melting point: 209° C.

$^{31}$P-NMR spectroscopy: (NaOD/D$_2$O) 19.13 ppm.

EXAMPLE 3

Preparation of tetraethyl 2-[(3,5-dichlorobenzoyl)(aminoiminomethyl)amino]ethane-1,1-bisphosphonate 650 mg (2.4 mmol) of (3,5-dichlorobenzoyl)-(aminoiminomethyl)amine and 730 mg (2.4 mmol) of tetraethyl vinyldiphosphonate are dissolved in 30 ml of toluene and 6 ml of dimethylformide (DMF). To this is added 0.17 g (2.4 mmol) of dry potassium carbonate, and the mixture is heated to boiling for 21 hours. The reaction solution is subsequently filtered and concentrated in a rotary evaporator. 1.8 g of crude product are obtained. The substance is purified on a silica gel column. Acetone is used as eluent.

Yield: 450 mg (35% of theory)

Melting point: 146° to 149° C.

$^{31}$P-NMR spectroscopy: (CDCl$_3$) 21.73 ppm.

EXAMPLE 4

Preparation of 2-[(3,5-dichlorobenzoyl)-(aminoiminomethyl)amino]ethane-1,1-bisphosphonic acid 350 mg (0.62 mmol) of tetraethyl 2-[(3,5-diohlorobenzoyl)-(aminoiminomethyl)amino]ethane-1,1-bisphosphonate are dissolved in 20 ml of acetonitrile. To this are added under argon 0.3 g of sodium iodide and 0.41 ml (3.10 mmol) of bromotrimethylsilane. The mixture is stirred at room temperature for 16 hours and subsequently at 40° C. for 1 hour. The sodium bromide which has formed is subsequently filtered off, and the solvent and volatiles are removed from the mother liquor at 40° C./0.1 torr. 20 ml of methylene chloride are added to the residue, and the solid which as formed is again filtered off with suction. The methylene chloride is removed at 40° C./0.1 torr. 15 ml of water subsequently added, and the mixture is stirred at room temperature for 15 minutes. The water is removed at 60° C./12 torr. 10 ml of isopropanol are then added to the resulting residue, and about 1 to 2 ml of water are added. The mixture is heated for 5 minutes. After cooling, the colorless crystals are filtered off with suction and dried in vacuo under 12 torr.

Yield: 170 mg (60%)

Melting point: 267° C.

$^{31}$P-NMR spectroscopy: (NaOD/D$_2$O) $\delta^{31}$P=19.09 ppm $^1$H-NMR spectroscopy: (NaOD/D$_2$O) $\delta$=1.90 (tt, $^2J_{PH}$=14 Hz, $^3J_{HH}$=6 Hz, 1H); 3.48 (td, $^3J_{PH}$=14 Hz, $^3J_{HH}$=6 Hz, 2H); 7.45 (s, 1H); 7.54 (s, 2H).

$^{13}$C-NMR spectroscopy: (NaOD/D$_2$O) $\delta$43.8 (C-1); 44.1 (C-2); 129.9 (C-3'); 133.0 (C-4); 136.7 (C-5, C-5'); 142.0 (C-6); 162.5 (C-Gua); 174.9 (C=0).

MS: m/e=419

EXAMPLE 5

Preparation of tetraethyl 2-[(1-methyl-2-indolylcarbonyl)-(aminoiminomethyl)amino]ethane-1,1-bisphosphonate 1.0 g (3.9 mmol) of 1-methyl-2-indolylcarbonylguanidine hydrochloride and 1.2 g (4 mmol) of tetraethyl vinyldiphosphonate are dissolved in 40 ml of tetrahydrofuran (THF) and 15 ml of dimethylformamide (DMF). To this is added 0.55 g (4 mmol) of dry potassium carbonate, and the mixture is heated to boiling for 21 hours. The reaction solution is subsequently filtered and concentrates in,a rotary evaporator. 2.0 g of crude product are obtained. The substance is purified on a silica gel column. Ethanol is used as eluent.

Yield: 1.4 g (70% of theory)

$^{31}$P-NMR spectroscopy: (CDCl$_3$) $\delta$=21.98 ppm

EXAMPLE 6

Preparation of 2-[(1-methyl-2-indolylcarbonyl)-(aminoiminomethyl)amino]ethane-1,1-bisphosphonic acid 1 g (1.8 mmol) of tetraethyl 2-[(1-methyl-2-indolylcarbonyl)-(aminoiminomethyl)amino]ethane-1,1-bisphosphonate from Example 5 is dissolved in 40 ml of acetonitrile. To this are added under argon 0.6 g of sodium iodide and 1.2 ml (90 mmol) of bromotrimethylsilane. The mixture is stirred at room temperature for 16 hours and subsequently at 40° C. for 1 hour. The sodium bromide which has formed is subsequently filtered off, and the solvent and volatiles are removed from the mother liquor at 40° C./0.1 torr. 20 ml of methylene chloride are added to the residue, and the solid which has formed is again filtered off with suction. The methylene chloride is removed at 40° C./0.1 torr. 15 ml of water are subsequently added, and the mixture is stirred at room temperature for 15 minutes. The water is removed at 60° C./12 torr. 10 ml of isopropanol are then added to the resulting residue, and about 1 to 2 ml of water are added. The mixture is heated for 5 minutes. After cooling, the colorless crystals are filtered off with suction and dried under 12 torr.

Yield: 300 mg (38%)

$^{31}$P-NMR spectroscopy: (NaOD/D$_2$O) $\delta^{31}$P=18.07 ppm $^1$H-NMR spectroscopy: (NaOD/D$_2$O) $\delta$=1.98 (tt, $^2J_{PH}$=14 Hz, $^3J_{HH}$=6 Hz, 1H); 3.65 (td, $^3J_{PH}$=14 Hz, $^3J_{HH}$=6 Hz, 2H); 7.08 to 8.56 (aromatic H, 5).

$^{13}$C-NMR spectroscopy: (NaOD/D$_2$O) $\delta$=32.5 (C-1); 41.8 (C-2); 41.9 (C-3);. 103.2 (C-4); 105.2 (C-5); 120.2 (C-6); 122.0 (C-7); 124.1 (C-8); 126.2 (C-9); 137.8 (C-10); 139.2 (C-11); 139.7 (C-12); 160.8 (C-Gua); 172.2 (C=0).

MS: m/e=419

EXAMPLE 7

Preparation of tetraethyl 2-[(3-methylsulfonyl-4-phenoxybenzoyl)-(aminoiminomethyl)amino]ethane-1,1-bisphosphonate 1.8 g (4.86 mmol) of (3-methylsulfonyl-4-phenoxybenzoyl)-(aminoiminomethyl)amine and 1.46 g (4.86 mmol) of tetraethyl vinyldiphosphonate are reacted as described in Example 1.

The substance is chromatographed on a silica gel column. Ethyl acetate:acetone =1:1 is used as eluent.

Yield: 800 mg (26%)

Melting point: 145° C.

$^{31}$P-NMR spectroscopy: (CDCl$_3$) $\delta^{31}$P=22.10 ppm $^1$H-NMR spectroscopy: (CDCl$_3$) $\delta$=1.35 (t, 12H); 3.31 (s, 3H); 4.0 (mc, 2H) 4.20 (mc, 9H); 6.88 (d, 1H); 7.13 (mc, 2H); 7.24 (mc, 1H); 7.42 (mc, 2H); 8.35 (d, 1H); 8.89 (s, 1H) ppm.

$^{13}$C-NMR spectroscopy: (CDCl$_3$) $\delta$=16.43; 29.30; 37.89; 43.36; 53.87; 63.14; 117.25; 120.36; 125.33; 129.72; 130.25; 155.06; 157.82; 175.0 ppm.

EXAMPLE 8

Preparation of tetraethyl 2-[(3-methylsulfonyl-4-N, N-diethylaminobenzoyl)-(aminoiminomethyl)amino] ethane-1,1-bisphosphonate 1.0 g (2.9 mmol) of (3-methylsulfonyl-4-N,N-diethylaminobenzoyl)-(aminoiminomethyl)amine and 0.9 g (2.9 mmol) of tetraethyl vinyldiphosphonate are reacted as described in Example 1.

The substance is chromatographed on a silica gel column. Ethyl acetate:acetone =1:1 is used as eluent.

Yield: 1.2 g (66.6%)

Melting point: 121° C.

$^{31}$P-NMR spectroscopy: (CDCl$_3$) $\delta^{31}$P=22.12 ppm $^1$H-NMR spectroscopy: (CDCl$_3$) $\delta$=1.07 (t, 6H); 1.35 (t, 12H); 3.18 (q, 4H); 3.34 (s, 3H); 3.98 (mc, 2H); 4.20 (mc, 9H); 7.32 (d, 1H); 8.36 (d, 1H); 8.92 (s, 1H) ppm.

$^{13}$C-NMR spectroscopy: (CDCl$_3$) $\delta$=12.09; 16.38; 38.20; 42.59; 48.37; 63.34; 124.46; 137.21; 136.99; 153.34; 175.64 ppm.

EXAMPLE 9

Preparation of 2-[(3-methylsulfonyl-4-phenoxybenzoyl)(aminoiminomethyl)amino]ethane-1,1-bisphosphonic acid 350 mg (0.55 mmol) of tetraethyl 2-[(3-methylsulfonyl-4-phenoxybenzoyl)-(aminoiminomethyl)amino]ethane-1,1-bisphosphonate from Example 7 are reacted as described in Example 2.

The product after hydrolysis with 40 ml of water is filtered off with suction and washed with 30 ml of acetone.

Yield: 150 mg (52.4%)

Melting point: 242° C.

$^{31}$P-NMR spectroscopy: (NaOD/D$_2$O) $\delta^{31}$P=17.65 ppm $^1$H-NMR spectroscopy: (NaOD/D$_2$O) $\delta$=2.04 (tt, 1H); 3.50 (s, 1H); 3.65 (td, 2H); 7.06 (d, 1H); 7.26 (d, 2H); 7.38 (mc, 1H); 7.54 (mc, 2H); 8.20 (mc, 1H); 8.55 (m, 1H) ppm.

EXAMPLE 10

Preparation of 2-[(3-methylsulfonyl-4-N,N-diethylaminobenzoyl)-(aminoiminomethyl)amino] ethane-1,1-bisphosphonic acid 600 mg (0.92 mmol) of tetraethyl 2[(3-methylsulfonyl-4-N,N-diethylaminobenzoyl)-(aminoiminomethyl)amino]-ethane-1,1-bisphosphonate from Example 8 are reacted as described in Example 2.

After hydrolysis with 30 ml of water, the product is filtered off with suction and subsequently mixed with acetone.

Yield: 483 mg (100%)

Melting point: 181° C.

$^{31}$P-NMR spectroscopy: (NaOD/D$_2$O) $\delta$=17.70 ppm ($^2J_{PH}$20.9 Hz; $^3J_{HH}$=14.2 Hz)

$^1$H-NMR spectroscopy: (NaOD/D$_2$O) $\delta$=1.03 (t, 6H); 2.11 (tt, 1H); 3.12 (q, 4H); 3.53 (s, 3H); 3.65 (td, 2H); 7.58 (d, 1H); 8.26 (mc, 1H); 8.58 (m, 1H) ppm.

EXAMPLE 11

The activity of the compounds according to the invention is demonstrated in vitro in the following experiments.

Bone resorption is determined by analyzing the release of $^{45}$Ca from the crania of 20-day old fetal rats. The bones are labeled by injecting 200 µCi/kg $^{45}$CaCl$_2$ into pregnant rats 2 days before the cranium of the fetuses is dissected.

1. Cultivation of the bones

The cranium of the fetuses is divided into two halves. One half of the cranium acts as control and the other half is incubated with the compounds according to the invention. Each half of the skull is cultivated in a sterile plastic dish. The cultivation medium (BGJb medium, Gibco) contains 10% fetal calf serum, penicillin/streptomycin (100,000 units/l, Gibco) and ascorbic acid (50 mg/l). The halves of the skulls are incubated at 37° C. in a gas atmosphere composed of 5% CO$_2$ and 95% O$_2$. After 48 hours, the cultivation medium is replaced by fresh medium, the compounds according to the invention and parathyroid hormone (10$^{-7}$M) are added, and incubation is continued for 48 hours. Parathyroid hormone (10$^{-7}$M Sigma) is added to the control. At the end of the experiment the $^{45}$Ca activity in the culture medium and in the bone is determined.

The results in Table 1 show the inhibition of release of $^{45}$Ca into the culture medium in percent. The results are the average of 3 to 5 experiments.

TABLE 1

| Product | Inhibition of release of $^{45}$Ca Concentration of the products | | |
|---|---|---|---|
| | 10$^{-10}$ | 10$^{-8}$M | 10$^{-6}$M |
| Example 4 | | 7% | 21% |
| Example 6 | | 22% | 29% |
| Example 9 | 22% | 21% | not tested |

We claim:

1. A compound of the tautomeric formula Ia, Ib or Ic

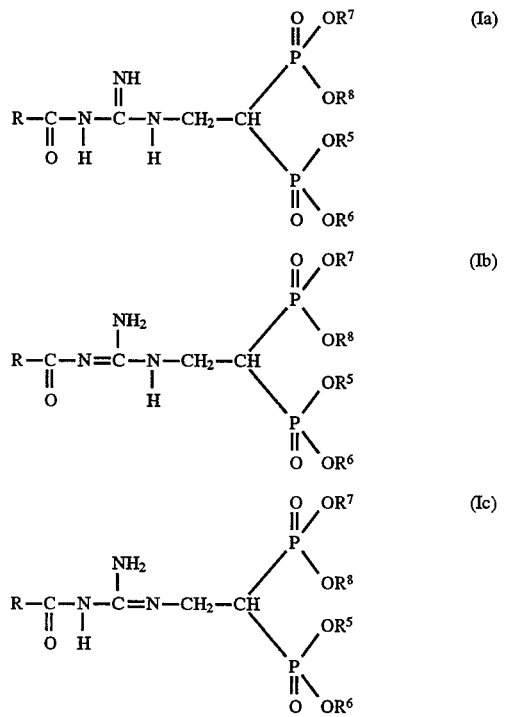

or a physiologically tolerated salt of said compound wherein R has the following meaning:

I) a radical of the formula V

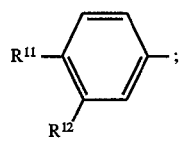
(V)

wherein one of $R^{11}$ or $R^{12}$ has the following meaning:

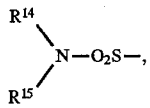

wherein $R^{14}$ and $R^{15}$ form with the nitrogen atom to which they are bonded a dihydroindole, and the other sustituent $R^{11}$ or $R^{12}$ in each case means

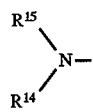

wherein $R^{14}$ and $R^{15}$ have the above-mentioned meaning, or

III) a radical of the formula VII

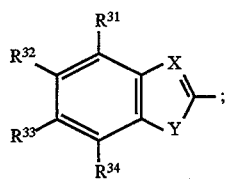
(VII)

wherein $R^{31}$, $R^{32}$, $R^{33}$ or $R^{34}$ has the following meaning:
1) hydrogen,
2) halogen,
3) —CN,
4) —$NO_2$,
5) —$N_3$,
6) —($C_1$-$C_6$)-alkyl, straight-chain or branched, or
7) $R^{35}$—$C_nH_{2n}$—Z—, wherein
  n is the number zero, 1, 2, 3, 4, 5 or 6, and the alkylene chain —$C_nH_{2n}$— is straight-chain or branched, and one carbon atom may be replaced by an oxygen, sulfur or nitrogen atom, and
  $R^{35}$ is
    1) hydrogen,
    2) ($C_3$-$C_6$)-alkenyl,
    3) ($C_5$-$C_8$)-cycloalkyl,
    4) ($C_5$-$C_8$)-cycloalkyl, substituted by a hydroxyl group or one methylene group is replaced by an oxygen, sulfur or nitrogen atom, or
    5) phenyl, unsubstituted or substituted by 1 to 3 radicals selected from the group consisting of
      5.1) halogen,
      5.2) $CF_3$,
      5.3) $CH_3$, —S(O)$_x$, wherein x is the number zero, 1 or 2,
      5.4) $R^{36}$—$W_y$, wherein $R^{36}$ is hydrogen, methyl or ethyl, W is oxygen, NH or $NCH_3$, and y is zero or 1,
      5.5) $C_mF_{2m+1}$, wherein m is the number 1, 2 or 3,
Z is
  1) —CO—,
  2) —$CH_2$—,
  3) —{CH(OH)}$_q$—, wherein q is the number 1, 2 or 3,
  4) —{C($CH_3$)(OH)}$_q$—, wherein q is the number 1, 2 or 3,
  5) —O—,
  6) —NH—, 7) 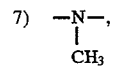

8) —S(O)$_x$—, wherein x is zero, 1 or 2,
  9) —$SO_2$—NH—, or

10) 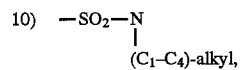

x is C—$R^{37}$, wherein $R^{37}$ is hydrogen, ($C_1$-$C_4$)-alkyl or ($C_2$-$C_4$)-alkenyl,
y has the following meaning
  a) NH,
  b) —N—($C_1$-$C_6$)-alkyl, or
  c) —N—($C_2$-$C_4$)-alkenyl and
$R^5$, $R^6$, $R^7$ and $R^8$ are identical or different and independently of one another are
  1) hydrogen,
  2) ($C_1$-$C_5$)-alkyl, straight-chain or branched, or
  3) phenyl.

2. A compound of the formula Ia, Ib or Ic as claimed in claim 1, or a physiologically tolerated salt of said compound, wherein R has the following meaning:
III) a radical of the formula VII wherein $R^{31}$, $R^{32}$, $R^{33}$ or $R^{34}$ has the following meaning:
  a) hydrogen,
  b) halogen, such as fluorine, chlorine, bromine or iodine,
  c) ($C_1$-$C_6$)-alkyl, straight-chain or branched, or
  d) $R^{35}$—$C_nH_{2n}$—Z—, wherein
    n is the number zero, 1 or 2, and the alkylene chain —$C_nH_{2n}$ is straight-chain or branched, and one carbon atom can be replaced by an oxygen, sulfur or nitrogen atom, and
  $R^{35}$ is
    1) hydrogen,
    ($C_5$-$C_8$)-cycloalkyl,
    ($C_5$-$C_8$)-cycloalkyl, substituted by a hydroxyl group, or one methylene group iS replaced by an oxygen, sulfur or nitrogen atom, or
    4) phenyl, unsubstituted or substituted by 1 to 3 radicals from the group
      4.1 halogen such as fluorine, chlorine, bromine or iodine,
      4.2 $CF_3$,
      4.3 $CH_3$—S(O)$_x$, wherein x is the number zero, 1 or 2,
      4.4 $R^{36}$—$W_y$, wherein $R^{36}$ is hydrogen, methyl or ethyl, W is oxygen, NH or $NCH_3$, and y is zero or 1,
      4.5 $C_mF_{2m+1}$, wherein m is the number 1, 2 or 3,
      4.6 pyridyl,
      4.7 quinolyl, or
      4.8 isoquinolyl,
Z is
  1) —CO—,
  2) —$CH_2$—,
  3) —{CH(OH)}q—, wherein q is the number 1, 2 or 3, 4) —{C(CH₃)(OH)}$_q$—, wherein q is the number 1, 2 or 3, 5) —(O)—, or 6) —S(O)$_x$—, wherein x is zero, 1, or 2, X is CH Y has the following meaning 1) —N—(C₁–C₆)-alkyl, or
2) —N—(C₂–C₄)-alkenyl, $R^5$, $R^6$, $R^7$ and $R^8$ are identical or different and independently of one another are 1) hydrogen, or 2) (C₁–C₅)-alkyl, straight-chain or branched.

3. Tetraethyl 2-{(1-methyl-2-indolylcarbonyl)-(aminoimonomethyl)amino}ethane-1,1-bisphosphonate, or 2-{(1-methyl-2-indolylcarbonyl)-(aminoiminomethyl)-amino}ethane-1,1-bisphosphonic acid.

4. A pharmaceutical composition containing an effective amount of a compound of a formula Ia, Ib or Ic of claim 1, or a physiologically tolerated salt of said compound, in addition to a pharmaceutically acceptable and physiologically tolerated ancillary substance or excipient, or diluent.

5. A method for the treatment of degenerative disorders of the bone system which method comprises administering the pharmaceutical composition of claim 4, wherein said degenerative disorder of the bone system is Paget's disease, metastatic osteocarcinoma, hypercalcemia or osteoporosis.

6. A method for the treatment of degenerative disorders of the bone system which method comprises administering an effective amount of a compound of formula Ia, Ib, or Ic of claim 1, wherein said degenerative disorder of the bone system is Paget's disease, metastatic osteocarcinoma, hypercalcemia or osteoporosis.

* * * * *

UNITED STATES PATENT AND TRADEMARK OFFICE
CERTIFICATE OF CORRECTION

PATENT NO. : 5,661,174

DATED : August 26, 1997

INVENTOR(S) : Christoph NAUMANN et al.

It is certified that error appears in the above-indentified patent and that said Letters Patent is hereby corrected as shown below:

Claim 1, column 17, line 18, "sustituent" should read --substituent--.

Claim 1, column 18, line 24, after "—N—$(C_2-C_4)$-alkenyl" insert --,--.

Claim 2, column 18, line 45, before "$(C_5-C_8)$-cycloalkyl", insert --2)--.

Claim 2, column 18, line 46, "$(C_5-C_8)$-cycloalkyl," should read --3) $(C_5-C_8)$-cycloalkyl,--.

Claim 2, column 18, line 47, "iS" should read --is--.

UNITED STATES PATENT AND TRADEMARK OFFICE
CERTIFICATE OF CORRECTION

PATENT NO. : 5,661,174
DATED : August 26, 1997
INVENTOR(S) : Christoph NAUMANN et al.

It is certified that error appears in the above-identified patent and that said Letters Patent is hereby corrected as shown below:

Claim 3, column 19, line 14, "(aminoimonomethyl)" should read --(aminoiminomethyl)--.

Signed and Sealed this

Seventh Day of July, 1998

Attest:

BRUCE LEHMAN

Attesting Officer

Commissioner of Patents and Trademarks